United States Patent
Weston et al.

(10) Patent No.: US 11,648,334 B2
(45) Date of Patent: May 16, 2023

(54) BONE GEL SHEET COMPOSITION AND METHOD OF MANUFACTURE

(71) Applicant: Vivex Biologies Group, Inc., Atlanta, GA (US)

(72) Inventors: Wendy W. Weston, Miami, FL (US); Silvia Daniela Gonzales, Miami, FL (US); Edgar S. Maldonado, Miami, FL (US)

(73) Assignee: Vivex Biologies Group, Inc., Atlanta, GA (US)

( * ) Notice: Subject to any disclaimer, the term of this patent is extended or adjusted under 35 U.S.C. 154(b) by 359 days.

(21) Appl. No.: 16/878,876

(22) Filed: May 20, 2020

(65) Prior Publication Data

US 2020/0282110 A1    Sep. 10, 2020

Related U.S. Application Data

(60) Division of application No. 15/236,807, filed on Aug. 15, 2016, now Pat. No. 11,253,629, which is a continuation-in-part of application No. 15/136,383, filed on Apr. 22, 2016.

(51) Int. Cl.
*A61L 27/36* (2006.01)
*A61L 27/22* (2006.01)
*A61F 2/28* (2006.01)

(52) U.S. Cl.
CPC ......... *A61L 27/3608* (2013.01); *A61L 27/222* (2013.01); *A61L 27/365* (2013.01); *A61L 27/3683* (2013.01); *A61L 27/3691* (2013.01); *A61F 2002/2835* (2013.01); *A61L 2430/02* (2013.01); *A61L 2430/40* (2013.01)

(58) Field of Classification Search
CPC ............... A61L 27/3608; A61L 27/365; A61L 27/3683; A61L 2430/02; A61L 2430/40
See application file for complete search history.

(56) References Cited

U.S. PATENT DOCUMENTS

| | | | |
|---|---|---|---|
| 3,458,397 A | 7/1969 | Myers et al. | |
| 4,172,128 A | 10/1979 | Thiele et al. | |
| 4,440,750 A | 4/1984 | Glowacki et al. | |
| 5,073,373 A | 12/1991 | Oleary et al. | |
| 5,236,456 A | 8/1993 | Oleary et al. | |
| 5,486,359 A | 1/1996 | Caplan et al. | |
| 5,490,937 A | 2/1996 | VanReis | |
| 5,531,791 A | 7/1996 | Wolfinbarger | |
| 5,733,542 A | 3/1998 | Haynesworth et al. | |
| 5,899,939 A * | 5/1999 | Boyce | A61L 27/3608 523/113 |
| 6,432,436 B1 | 8/2002 | Gertzman et al. | |
| 6,437,018 B1 | 8/2002 | Gertzman et al. | |
| 6,458,375 B1 | 10/2002 | Gertzman et al. | |
| 6,576,249 B1 | 6/2003 | Gendler et al. | |
| RE38,522 E | 5/2004 | Gertzman et al. | |
| 6,911,212 B2 | 6/2005 | Gertzman et al. | |
| 6,998,135 B1 | 2/2006 | Sunwoo et al. | |
| 7,015,037 B1 | 3/2006 | Furcht et al. | |
| 7,019,192 B2 | 3/2006 | Gertzman et al. | |
| 7,045,141 B2 | 5/2006 | Merboth et al. | |
| 7,067,123 B2 | 6/2006 | Gomes et al. | |
| RE39,587 E | 4/2007 | Gertzman et al. | |
| 7,488,348 B2 | 2/2009 | Truncale et al. | |
| 7,659,118 B2 | 2/2010 | Furcht et al. | |
| 7,847,072 B2 | 12/2010 | Thorne | |
| 7,879,103 B2 | 2/2011 | Gertzman et al. | |
| RE42,208 E | 3/2011 | Truncale et al. | |
| 7,901,457 B2 | 3/2011 | Truncale et al. | |
| 8,075,881 B2 | 12/2011 | Verfaillie et al. | |
| RE43,258 E | 3/2012 | Truncale et al. | |
| 8,221,500 B2 | 7/2012 | Truncale et al. | |
| 8,292,968 B2 | 10/2012 | Truncale et al. | |
| 8,354,370 B2 | 1/2013 | Kopen et al. | |
| 8,394,419 B2 | 3/2013 | Borden | |
| 8,834,928 B1 | 9/2014 | Truncale et al. | |
| 9,138,508 B2 | 9/2015 | Borden | |
| 9,138,509 B2 | 9/2015 | Sunwoo et al. | |
| 9,192,695 B2 | 11/2015 | Shi | |
| 2003/0059414 A1 | 3/2003 | Ho et al. | |
| 2004/0058412 A1 | 3/2004 | Ho et al. | |
| 2005/0181502 A1 | 8/2005 | Furcht et al. | |
| 2006/0004189 A1 | 1/2006 | Gandy | |
| 2007/0049739 A1 | 3/2007 | Troxel | |
| 2007/0224177 A1 | 9/2007 | Ho et al. | |
| 2008/0008766 A1* | 1/2008 | Talton | A61L 27/222 424/490 |
| 2008/0281431 A1* | 11/2008 | Missos | A61L 27/427 623/23.6 |

(Continued)

OTHER PUBLICATIONS

Augat, P. et al. "The role of cortical bone and its microstructure in bone strength" (Age and Ageing 2006; 35-S2: ii27-ii31) (Year: 2006).*

Chu Chang Chua, Deborah Ceiman, and Roger L. Ladda; "Transforming Growth Factors Released From Kirsten Sarcoma Virus Transformed Cells do not Compete for Epidermal Growth Factor Membrane Receptors"; Journal of Cellular Physiology 117:116-122 (1983).

Yawei Liua, Anders Kalenb, Olof Ristob & ; "Time- and pH-dependent release of PDGF and TGF-B from platelets <emph type="2">in vitro</emph>"; pp. 233-237 Platelets vol. 14, Issue 4, 2003 ; Published online: Jul. 7, 2009.

Trinity Elite, product, sales brochure, TT-1515, Orthofix Holdings Inc, Oct. 2015.

(Continued)

*Primary Examiner* — Andrew S Rosenthal
(74) *Attorney, Agent, or Firm* — David L. King

(57) ABSTRACT

A bone gel composition consists of cortical bone. The cortical bone is made from cut pieces freeze-dried then ground into particles and demineralized then freeze-dried. A volume of the particles is placed in a solution of sterile water to create a mixture, the water volume being at least twice the particle volume, the mixture is autoclaved under heat and pressure to form a gelatin, the resulting bone gel is formed into sheets having a thickness (t).

7 Claims, 9 Drawing Sheets

(56) References Cited

U.S. PATENT DOCUMENTS

2013/0195810 A1    8/2013   Crawford et al.
2014/0005793 A1    1/2014   Koford et al.
2014/0030235 A1    1/2014   Vamey et al.
2015/0012107 A1    1/2015   Koford et al.
2016/0030639 A1    2/2016   Shi

OTHER PUBLICATIONS

Osteocel bone graft web page, http://www.nuvasive.com/patient-solutions/nuvasive-integrated-surgical-solutions/Jsteocel-bone-grafl/; 2016.

\* cited by examiner 10  20

10

10

10

Bone Gel Product Manufacturing Process Outline

BONE GEL SHEET COMPOSITION AND METHOD OF MANUFACTURE

RELATED APPLICATIONS

This application is a division of U.S. application Ser. No. 15/236,807 filed on Aug. 15, 2016 which is a continuation in part of co-pending U.S. application Ser. No. 15/136,383 filed on Apr. 22, 2016 entitled, "Bone Gel Composition And Method Of Manufacture".

TECHNICAL FIELD

This invention is a demineralized bone composition made in the form of a gel. More specifically, a composition that can be formed as a gel or gelatinous composition shaped into flat sheets and a method of manufacture and use of said composition.

BACKGROUND OF THE INVENTION

The manufacture and use of bone allografts from bone tissue is well known. The use of particles of various specific sizes and distributions have been determined to have beneficial characteristics for new bone growth in the treatment of osseous defects and bone voids.

The issue of getting the repair composition to stay in position has been addressed for various formulations made into malleable paste or putty by the addition of collagen or other gelatinous materials.

The present invention provides an improvement over those prior art materials by providing a bone gel that is conformable into sheets and configured to be shaped so it can be added to autograft or allograft bone particles to make a moldable bone product.

SUMMARY OF THE INVENTION

A bone gel composition consists of cortical bone. The cortical bone is made from cut pieces freeze-dried then ground into particles and demineralized then freeze-dried. A volume of the particles is placed in a solution of sterile water to create a mixture, the water volume being at least twice the volume of the freeze-dried particles, the mixture is autoclaved under heat and pressure to form a gelatin, the resulting bone gel is formed into sheets having a thickness (t) and frozen for later use, preferably frozen at a temperature of −20 to −80 degrees C. The cortical bone has the cut pieces having a width, a length and a thickness in the range of 1 to 4 mm. The cortical bone pieces are ground to a particle size up to 125 microns.

A method of making a bone gel composition consisting of cortical bone comprises the steps of: preparing cortical bone by cutting the cortical bone into pieces, freeze-drying the pieces and then grinding into particles and demineralizing the ground particles and freeze-drying the demineralized ground particles to form DBM particles; autoclaving a volume of the DBM particles mixed with sterile water in a 1:2 ratio by volume for a predetermined time at a pre-set temperature and pressure to form a gelatin; shaping the bone gel into a sheet having the thickness (t); cooling the gelatin to form a bone gel; cutting the sheet into small sheets of a polygonal shape, if necessary, preferably of a circular, square or a rectangular shape wherein the thickness is between 1 and 10 mm, preferably between 2 and 3 mm and packaging the resulting bone gel and storing the packaged bone gel.

Definitions

Cohesiveness is defined as the capacity of DBM aseptic paste to maintain its shape while immersed in normal saline or water for a minimum of one minute.

DBM—Demineralized Bone Matrix.

Freeze Dried/Lyophilized—Tissue dehydrated for storage by conversion of the water content of frozen tissue to a gaseous state under vacuum that extracts moisture.

Malleability is the ability to be molded into different shapes with no visible cracks.

Normal Saline—0.9% Sodium Chloride Solution.

PBS—Phosphate Buffered Saline.

SRI—an equipment sterilization company.

BRIEF DESCRIPTION OF THE DRAWINGS

The invention will be described by way of example and with reference to the accompanying drawings in which:

FIG. 5 is a photograph of the bone gel composition being worked with.

FIG. 6 is another photograph of the bone gel composition being worked with.

DETAILED DESCRIPTION OF THE INVENTION

The present invention encompasses the manufacturing of bone gel derived from human cadaveric cortical bone. Cortical bone is obtained from male or female donors within suitable age groups. Full body donors with no joint replacements are preferred. The donors' medical and social history are screened for medical conditions such as osteoporosis and alcohol abuse, which may hinder the intended purpose of the final product. At ambient temperature, bone gel is gelatinous and cohesive. Therefore, it is intended to serve as a binding agent. Bone gel is ready for use or can be mixed with other products.

Figure 1:
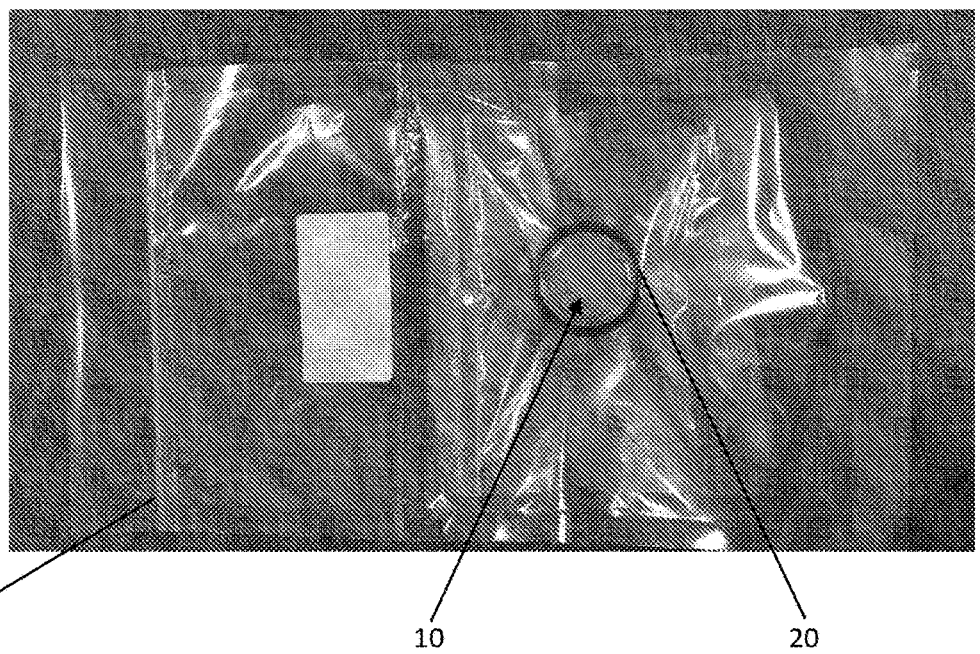
FIG. 1 shows a photograph of the bone gel composition in a container and packaged in a clear sealed bag.
Figure 2:
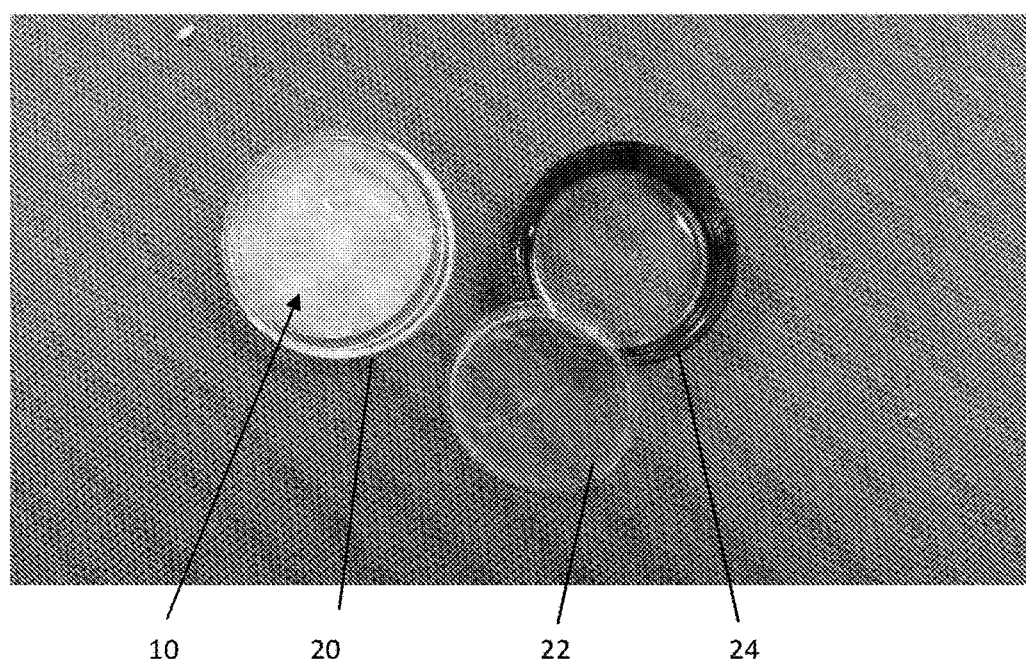
FIG. 2 is a photograph of the bone gel composition removed from the packaging with the container lid removed and open.
Figure 3:
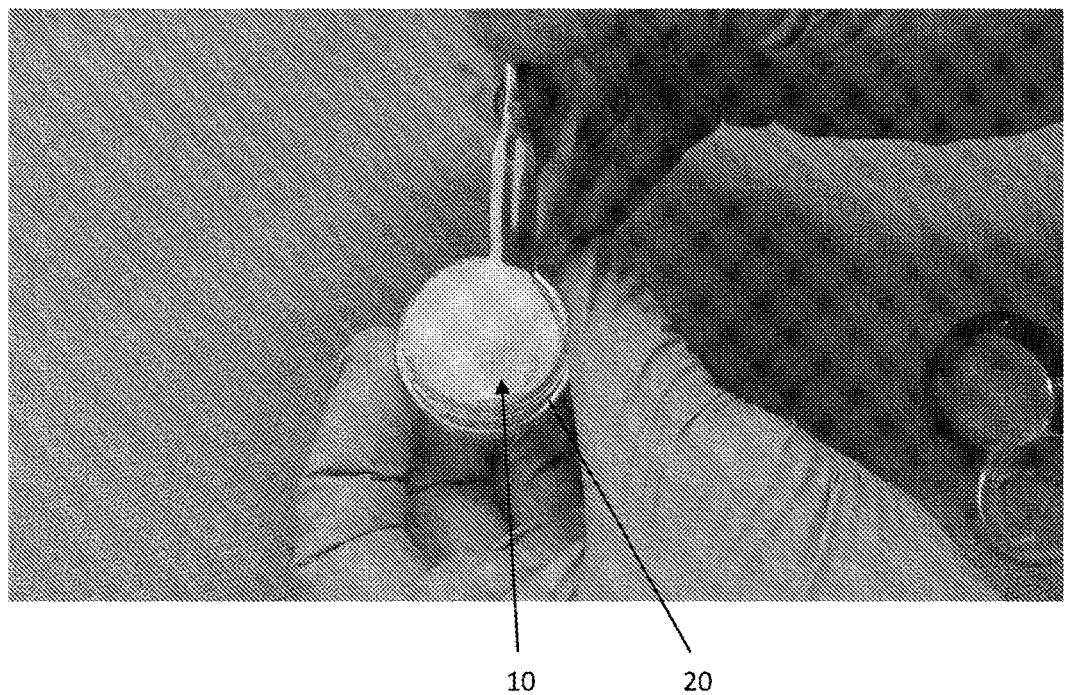
FIG. 3 is a photograph of the bone gel composition being removed from the container.
Figure 4:
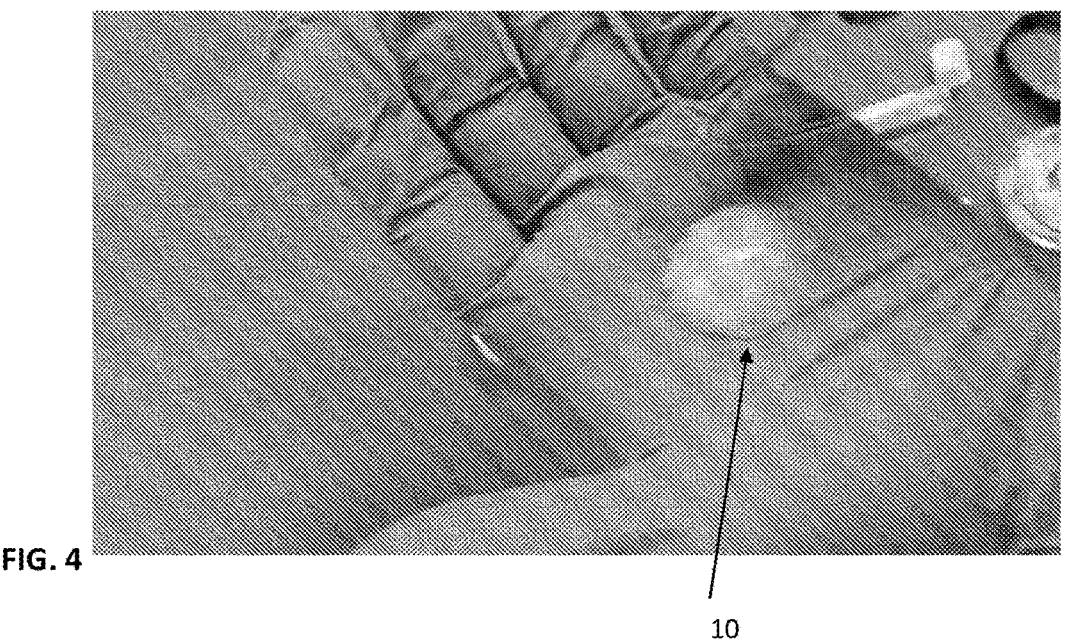
FIG. 4 is a photograph of the bone gel composition removed from the container.
Figure 5:
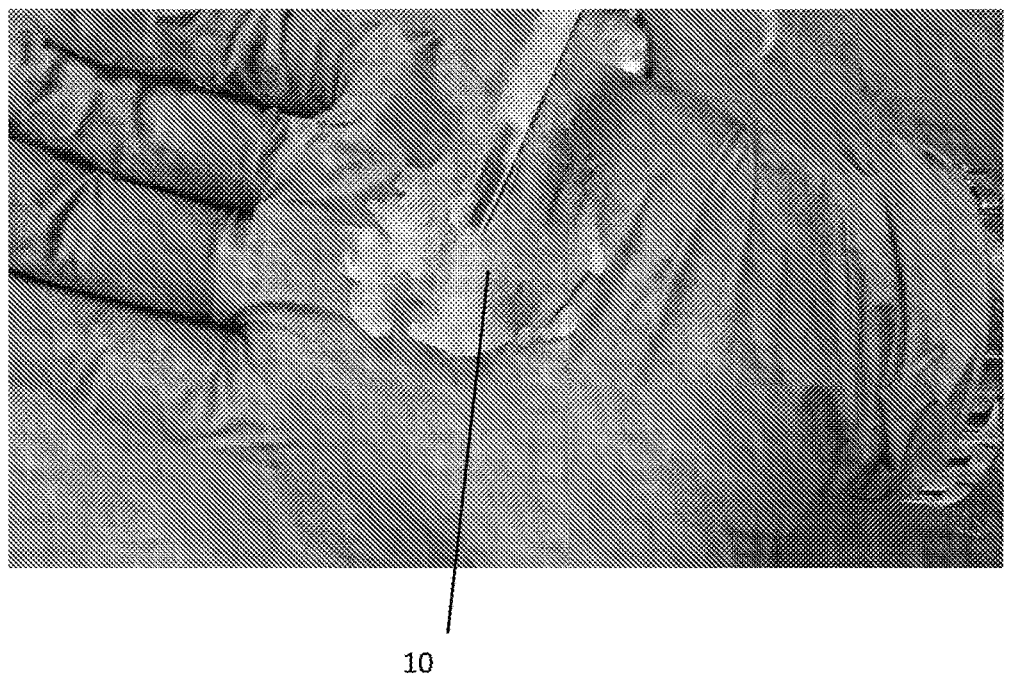
Figure 6:
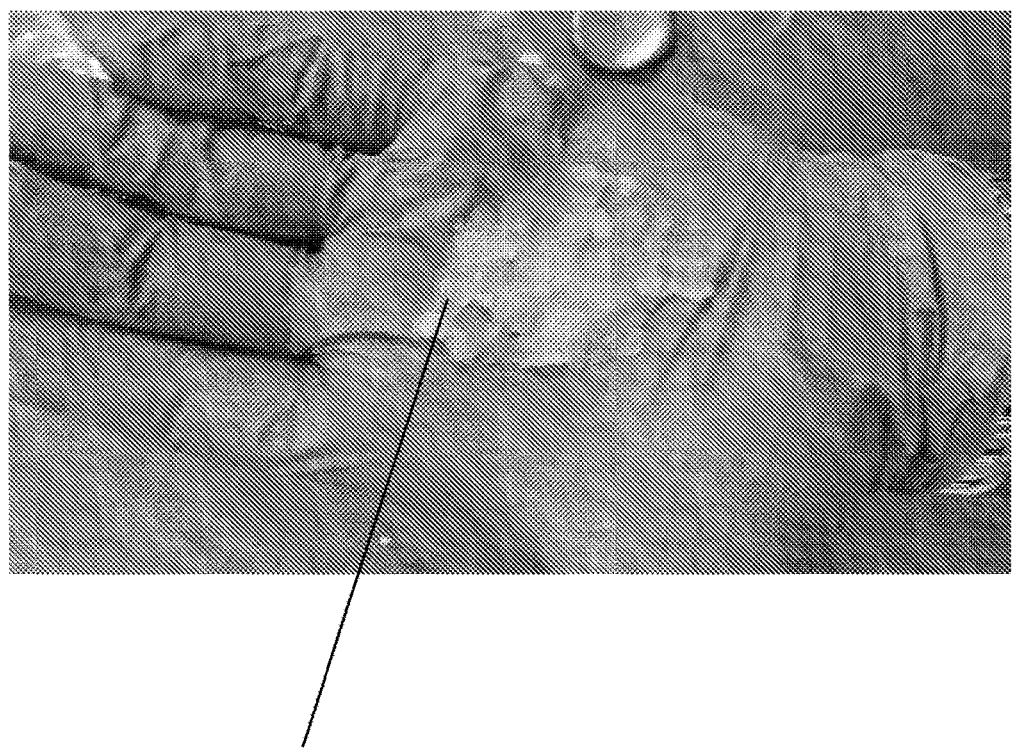

The bone gel product is entirely derived from cortical bone. The cortical bone is aseptically recovered, cleaned, cut, morselized or shaved, ground, sieved at different sizes, demineralized and freeze-dried to obtain cortical bone particles. Freeze dried, demineralized, ground cortical bone is then mixed with water. The mix is pressurized and heated to form the Bone Gel. Final Bone Gel 10 products of 2 cc, 4 cc or 8 cc are distributed into containers 20, packaged in final packaging 50, as shown in FIG. 1, and stored at room temperature or frozen until distribution to the end user. The amount of bone gel can vary depending on the application.

Figure 7:
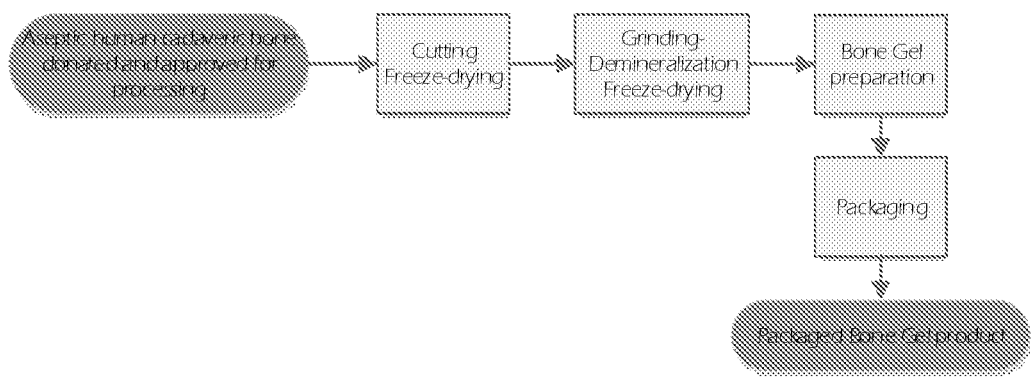
FIG. 7 is a schematic illustration of the bone gel product manufacturing process outline.

The overall manufacturing process for the Bone gel product can be seen in FIG. 7. The input of the process is the donated and approved for processing aseptic human cadaveric cortical bone immediately frozen after recovery. Once the cortical bone has been processed, the output is the packaged Bone gel product. The process itself has been divided into four subprocesses with their own respective inputs and outputs.

Figure 8:
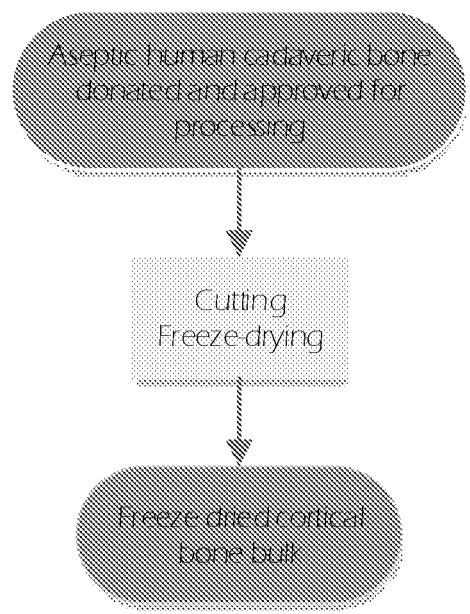
FIG. 8 is a schematic illustration of the subprocess of cutting and freeze-drying.

The cutting subprocess is schematically shown in FIG. 8.

Prior to cutting the donated and approved for processing human cadaveric cortical bone, all extraneous material such as muscle fibers, adipose tissue, and periosteum are removed from the tissue. Bones are then rinsed a minimum of 3 times with physiological grade Normal Saline (0.9% Sodium Chloride). Using a band saw, the bones are cut in a manner that the cortical and cancellous portions are separated.

The cortical bone is then cut into small pieces using a band saw. The small pieces are rinsed a minimum of three times in Normal Saline and then placed into a metal container with fresh Normal Saline. The container is aseptically wrapped, placed on a shaker and mechanically agitated for 5 to 10 minutes. The bone tissue is then morselized into 1 to 4 mm length and width pieces, respectively, using a morselizer. The tissue is rinsed again a minimum of three times with Normal Saline in order to remove any remnants of blood and/or fat deposits. The bone pieces are rinsed with hydrogen peroxide for no more than 10 minutes to remove fat/blood. The bone pieces are rinsed a minimum of three times with sterile water to remove any residual hydrogen peroxide. Then, the bone tissue is placed in a metal container and stored at −80° C. The frozen bone tissue is freeze dried with a cycle set for 33 hours and 50 minutes. It is understood the timing, ratios and volumes can vary based on the equipment and procedures used and the above is exemplary of the preferred process for the inventors' equipment.

Figure 9:
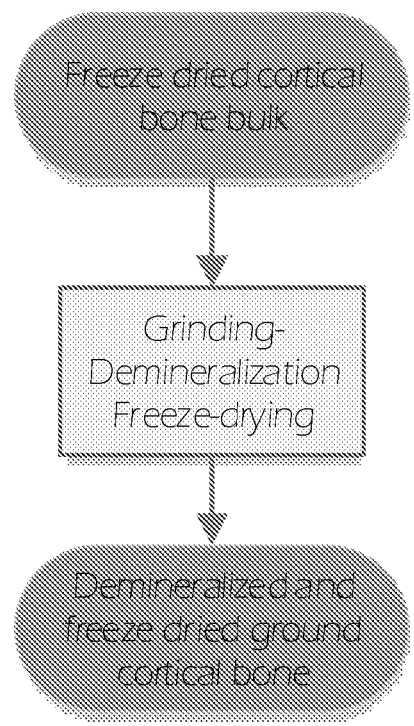
FIG. 9 is a schematic illustration of the subprocess of grinding, demineralization, freeze-drying.

The Grinding-Demineralization subprocess is shown in FIG. 9.

Once the freeze-drying cycle is completed, the cortical bulk is ground and sieved to obtain particle sizes of up to 125 μm, typically 25 to 125 μm. The particulate tissue is demineralized by addition of 0.6 HCL solution at a 20:1 ratio (20 ml of 0.6 HCL to 1 g of bone). The solution containing the tissue is placed on a magnetic stir plate for 19 minutes. After decanting the liquid, the particulate tissue is mixed with sterile water at a 20:1 ratio (20 ml of sterile water to 1 g of bone). The solution containing the tissue is placed on a magnetic stir plate for 4 minutes. The process of decanting, mixing and incubating for 4 minutes is repeated with PBS solution. After decanting the PBS, the particulate tissue is mixed with sterile water at a 20:1 ratio (20 ml of sterile water to 1 g of bone). The solution containing the tissue is placed on a magnetic stir plate for 9 minutes. The water waste solution is decanted and the demineralized particulate tissue is stored at −80° C. The frozen, demineralized particulate tissue is freeze dried for 33 hours 50 minutes. At the end of the freeze-drying process, samples can be collected for residual moisture and residual calcium testing. It is understood the timing, ratios and volumes can vary based on the equipment and procedures used and the above is exemplary of the preferred process for the inventors' equipment.

Figure 10:
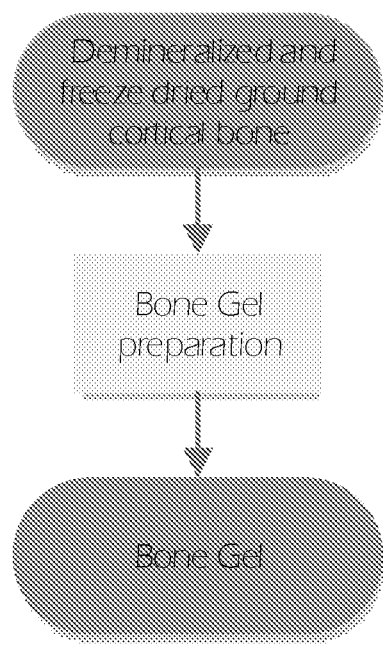
FIG. 10 is a schematic illustration of the subprocess of bone gel preparation.

The Bone Gel Preparation subprocess is shown in FIG. 10.

The demineralized, freeze-dried cortical bone particles can be divided into groups of 100 cc, approximately. Each group is placed in a Pyrex glass bottle and mixed with sterile water. The ratio of sterile water to particles is 2:1 by volume. In order to prepare Bone Gel, the mix is autoclaved for 1.25 hours. The autoclaving process includes conditioning (15 minutes), exposure (30 minutes) and drying (30 minutes). Temperature during the exposure step is 121.1° C. and the pressure is 30.15 psi. After autoclaving is completed, the Bone Gel is aliquoted to jars or in trays. It is understood the timing, ratios and volumes can vary based on the equipment and procedures used and the above is exemplary of the preferred process for the inventors' equipment.

Figure 11:
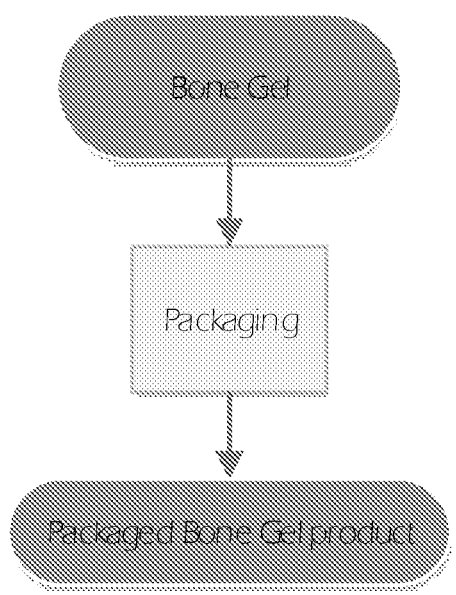
FIG. 11 is a schematic illustration of the subprocess of packaging.

The Packaging subprocess is shown in FIG. 11.

The Bone Gel is packaged in closed containers. The containers have a lid insert 22 secured by a cap 24 or is packaged in tear pouches 52 followed by outer packing. The packaged final products are stored at room temperature or frozen until they are distributed to the end user. Batch release is contingent upon final culture results.

The bone gel composition is designed to be mixed with allograft or autograft bone particles, strands, growth factors, bone putty, bone paste, cells, or other bone growth enhancing products.

Figure 12:
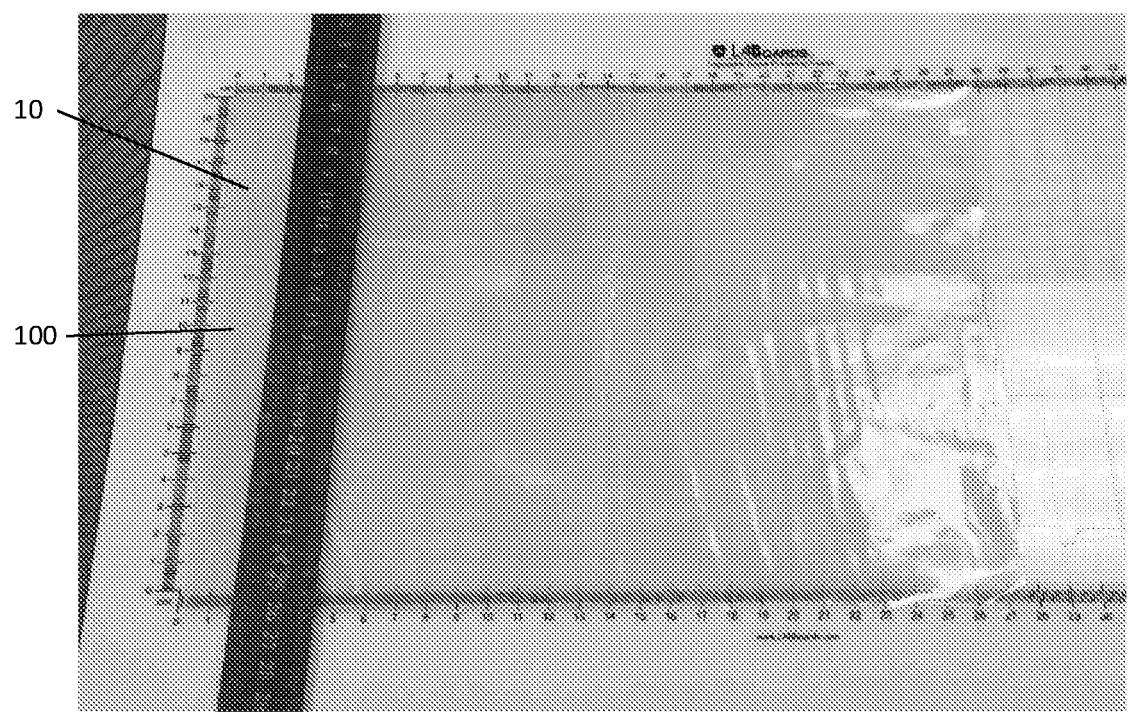
FIG. 12 is a photograph of the bone gel composition formed as a sheet material of the present invention.
Figure 13A:
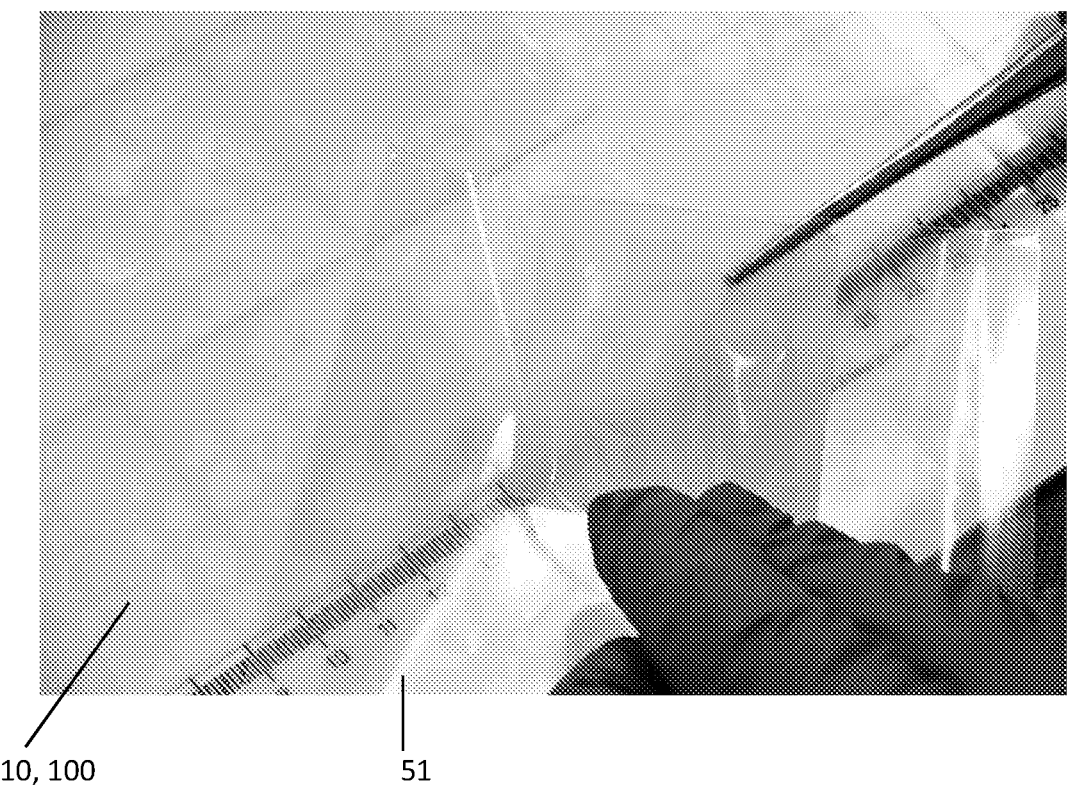
FIG. 13A is photograph of the sheet material being cut into rectangular or square polygonal shapes.
Figure 13B:
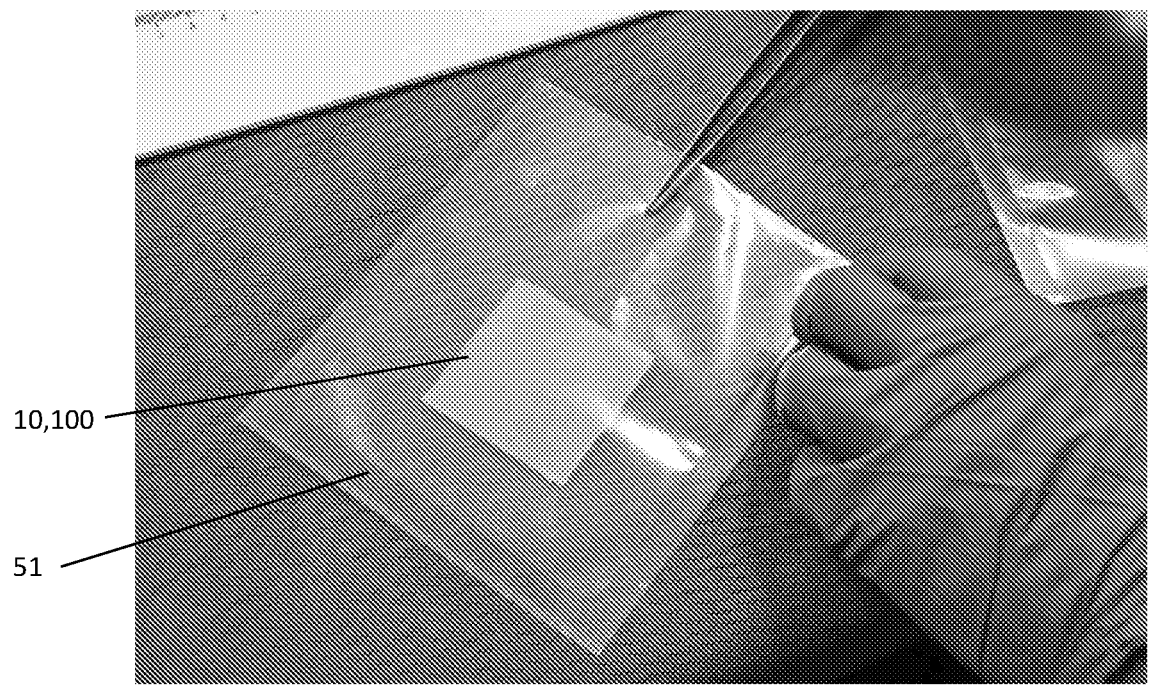
FIG. 13B is a photograph of the rectangular or square shaped sheet being put in a bag for packaging.

With reference to FIG. 12, the bone gel composition 10 is shown formed as a thin sheet 100 of material having a thickness t. The bone gel 10, as shown in FIG. 12, was flattened into a substantially rectangular sheet approximately 20 cm in width by approximately 25 to 27 cm in length. After the material was formed in large rectangular shapes, it can then be cut into smaller polygonal shapes, as illustrated in FIG. 13A. In FIG. 13A, a corner of the bone gel sheet 100 has been cut into a substantially square shape and, as shown in FIG. 13B, this substantially square shape is then placed in a sterile package 51 for later use.

Figure 14A:
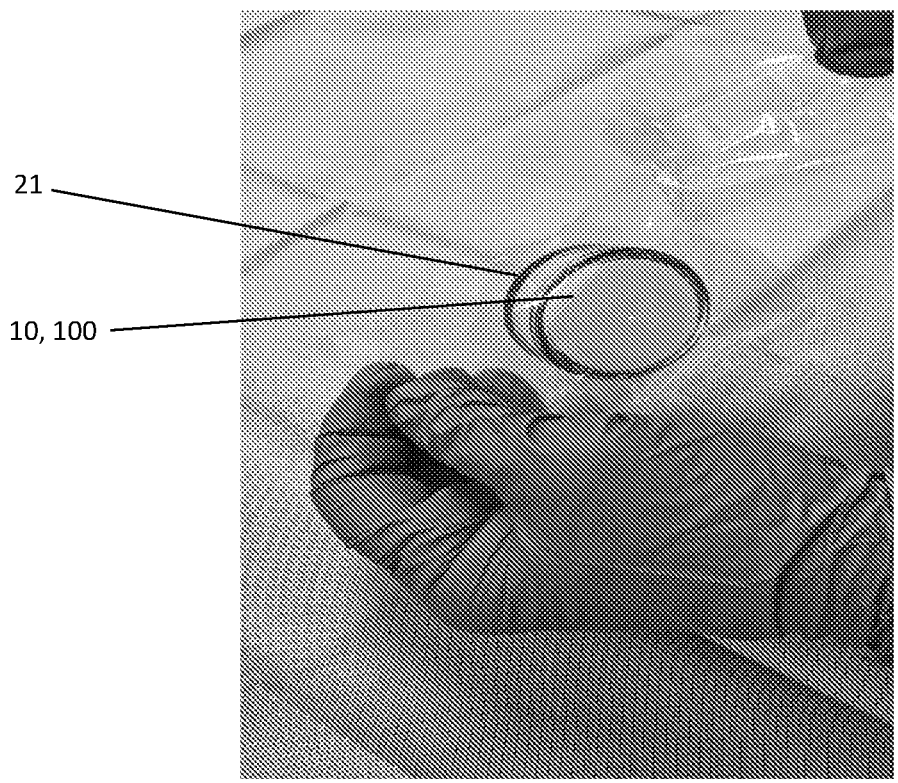
FIG. 14A is a photograph of the bone gel composition shaped as a round or circular sheet by being subprocessed in a round mold or container.
Figure 14B:
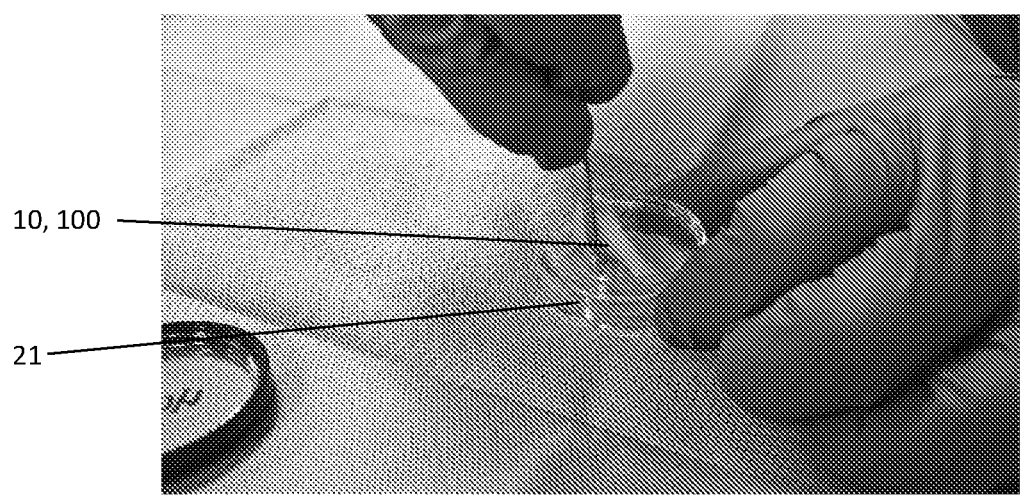
FIG. 14B is a photograph of the bone gel round sheet being removed from the container.
Figure 14C:
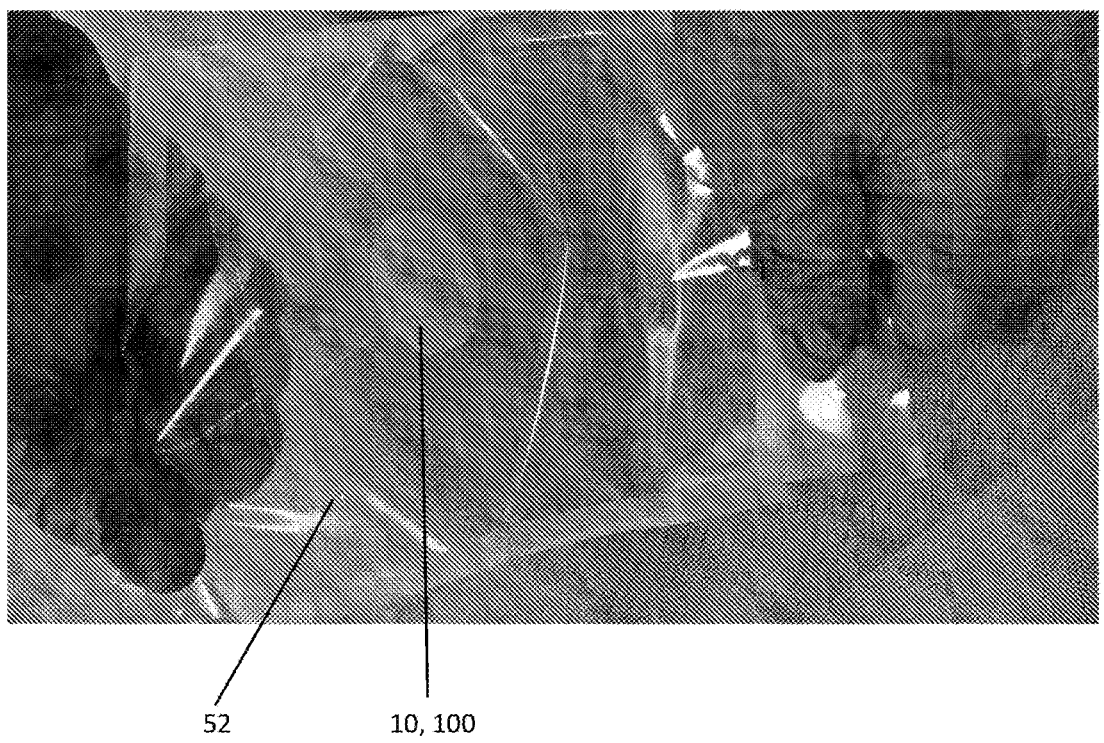
FIG. 14C is a photograph of the bone gel round sheet after being placed in a packaging bag.

In another configuration, small glass containers 21 can be utilized wherein the bone gel 10 is pressed into the circular shaped container 21 and flattened to the desired thickness t, as shown in FIG. 14A. Once properly sized and flattened, the material then can be lifted from the container 21, as shown in FIG. 14B. Once the material has been removed from the container 21, it then can simply be put in a sterile package 52, as illustrated in FIG. 14C.

The ability to take the bone gel 10 and flatten it into polygonal shapes such as square, rectangular, circular or any other desired shape, makes the material easier to handle for its particular applications allowing the surgeon to pick up a small, well defined structure and to place it in the area of the bone to be repaired or healed using this sheet like material 100. As shown, the material can be taken from the package and other material such as stem cells or other medicants can be added to the material to assist in its use in bone defect repairs.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A method of making a bone gel composition consisting of cortical bone comprises the steps of: preparing cortical bone by cutting the cortical bone into pieces, freeze-drying the pieces and then grinding into particles of a size up to 125 microns and demineralizing the ground particles and then freeze-drying the demineralized ground particles to form DBM particles;
   autoclaving a volume of the DBM particles mixed with sterile water in a 1:2 ratio by volume for a predetermined time at a pre-set temperature and pressure to form a gelatin, the gelatin consisting of the volume of the DBM particles and the sterile water;
   cooling the gelatin to form a bone gel;
   forming the bone gel into sheets of bone gel of a thickness (t), the thickness (t) being in the range of 1.0 to 10.0 mm;
   cutting the sheets of bone gel to a desired circular, semi-circular or polygonal shape; and
   freezing or packaging the cut sheets of bone gel, wherein the cut sheets of bone gel are frozen either before or after packaging, wherein the sheets of bone gel when cut into different shapes with no visible cracks maintains the cut shape while immersed in normal saline or water for a minimum of one minute.

2. The method of making a bone gel composition of claim 1 wherein the polygonal shape is a square or rectangle.

3. The method of making a bone gel composition of claim 2 wherein the polygonal shape is a rectangle.

4. The method of making a bone gel composition of claim 1 wherein the thickness (t) is in the range of 2 to 3 mm.

5. The method of making a bone gel composition of claim 3 wherein the rectangle has a predetermined width and a predetermined length.

6. The method of making a bone gel composition of claim 1 wherein the bone gel sheet is frozen at −20 to −80 degrees C.

7. The method of making a bone gel composition of claim 1 wherein the cortical bone has the cut pieces having a width, a length and a thickness in the range of 1 to 4 mm.

* * * * *